United States Patent
Sarver

(10) Patent No.: US 7,273,277 B2
(45) Date of Patent: Sep. 25, 2007

(54) ADVANCED VISION INTERVENTION ALGORITHM

(75) Inventor: Edwin Jay Sarver, Merritt Island, FL (US)

(73) Assignee: Sarver and Associates, Merritt Island, FL (US)

( * ) Notice: Subject to any disclaimer, the term of this patent is extended or adjusted under 35 U.S.C. 154(b) by 577 days.

(21) Appl. No.: 09/997,159

(22) Filed: Nov. 28, 2001

(65) Prior Publication Data

US 2002/0103479 A1    Aug. 1, 2002

Related U.S. Application Data

(60) Provisional application No. 60/250,296, filed on Nov. 30, 2000.

(51) Int. Cl.
*A61B 3/00* (2006.01)

(52) U.S. Cl. .......................... 351/200; 351/212; 356/2; 356/124; 356/128

(58) Field of Classification Search ................ 128/898; 356/2, 376, 124, 128, 348, 359, 360; 606/4; 434/262, 271
See application file for complete search history.

(56) References Cited

U.S. PATENT DOCUMENTS

| 4,721,379 A | | 1/1988 | L'Esperance |
| 5,092,880 A | | 3/1992 | Ohmi |
| 5,282,852 A | | 2/1994 | Capetan et al. |
| 5,430,506 A | | 7/1995 | Volk |
| 5,724,258 A | | 3/1998 | Roffman |
| 5,891,131 A | * | 4/1999 | Rajan et al. .................... 606/5 |
| 6,149,643 A | * | 11/2000 | Herekar et al. ................. 606/5 |

FOREIGN PATENT DOCUMENTS

WO    WO 00/13628    3/2000

OTHER PUBLICATIONS

Glassner, A.S., "An Introduction to Ray Tracing," Academic Press, Inc., (1991).
Hearn, D. and Baker, M.P., Computer Graphics, Second Edition, Prentice Hall, Inc. (1994).

(Continued)

*Primary Examiner*—Corrine McDermott
*Assistant Examiner*—Javier G. Blanco
(74) *Attorney, Agent, or Firm*—McHale & Slavin, P.A.

(57) ABSTRACT

A method of optimizing the predictability of a vision correction procedure by comparing historical data, including the vision defect, the correction method and outcome, in terms of wavefront aberrations with a patient's condition to select an acceptable procedure. The patient's eye is examined and an optical model is created and compared to the historical data to select an acceptable procedure. The procedure is performed and the outcome is included in the data base.

11 Claims, 4 Drawing Sheets

OTHER PUBLICATIONS

Celikkol et al., "Calculation of Intraocular Lens Power After Radial Keratotomy With Computerized Videokeratography", AmJ. Opthalmol. (1995); 120: pp. 739-750.

Hoffer: "IOL Power Calculation after Refractive Surgery". In: Refractive Surgery; Agarwal et al.: Jaypee Brothers Medical Publishers, (2000); pp.631-633.

Gimbel, Refractive Surgery, Slack, Inc., (2000).

Gimbel et al., "Refractive error in cataract surgery after previous refractive surgery", J. Cataract. Refract.Surg (2000) Jan.; 26.(1): pp. 142-144.

Glassner, A. S.; "An Introduction to Ray Tracing", Academic Press (1989).

Holladay et al., "A three-part system for refining intraocular lens power calculations", J.Cataract.Refract.Surg. Jan. (1988); vol. 14: pp. 17-24.

Holladay, JT: "Power Calculation and Optics of Phakic IOLs". In:The Implantable Contact Lens (ICL) and Other Phakic IOLs. Lovisolo et al., (1999); pp. 295-302.

Hong et al., "Longitudinal Evaluation of Optical Aberrations Following Laser in situ Keratomileusis Surgery", J.Cataract.Refract. Surg. (2000); 16(5):pp. 647-650.

Liang et al., "Objective measurement of wave aberrations of the human eyes with the use of a Hartmann-Shack wave-front sensor", J. Opt. Soc. Am.(A.) (1994); 11:pp. 1949-1957.

Seiler et al., "Operative Correction of Ocular Aberrations to Improve Visual Acuity", J.Cataract.Refract.Surg. (2000), 16(5): pp. 619-622.

Sarver et al., "Modeling and Predicting Visual Outcomes With VOL-3D", Journal of Refractive Surgery; (Thorofare, N.J.: 1995) United States Sep.-Oct. 2000; vol. 16; No. 5, Sep. 2000; pp. S611-S616.

Klonos et al., "A Computer Model for Predictin Image Quality After Photorefractive Keratectomy", Journal of Refractive Surgery, Thorofare, N.J.; vol. 12, No. 2, Feb. 1996; pp. S280-S284.

* cited by examiner

ADVANCED VISION INTERVENTION ALGORITHM

CROSS REFERENCE TO RELATED APPLICATION

This application is a continuation of Provisional Patent Application Ser. No. 60/250,296, filed Nov. 30, 2000.

FIELD OF THE INVENTION

This invention relates in general to the field of optically corrected aberrant human vision and more particularly, relates to the construct of an improved optical model of the human eye and procedures to achieve a more precise optical correction.

BACKGROUND OF THE INVENTION

The human eye often contains aberrations that may be optically corrected for normal activities. If the primary aberration causes a distant object to be focused in front of the retina, for example, the eye is said to be myopic or near-sighted. If the primary aberration causes the distant object to be focused behind the retina, the eye is said to be hyperopic or far-sighted. Often the aberrations are such that the light rays which enter the cornea in one location from a distant object focus at one point inside the eye while light rays which enter the cornea in another location from the same distant object focus at a different point inside the eye. A typical example of this is called astigmatism in which light rays which enter the eye in one meridian focus at one point and light rays which enter in the meridian perpendicular focus at another location. It is easy to visualize that other more general aberrations can and do occur in the human eye.

Interventions in common use today to correct such human eye aberrations are spectacles, contact tenses, corneal refractive surgery, such as LASIK or corneal implants, and phakic intraocular lenses. The correct specification of spherocylindrical spectacles and contact lenses is well established. The newer surgery based techniques are not as predictable as may be desired, but still are in wide spread use.

A current development is instruments intended to measure the total aberrations of the eye rather than simply the traditional spectacle correction parameters of sphere, cylinder, and axis. These instruments provide the theoretical information required to improve on vision correction beyond the lower-order aberrations of sphere, cylinder, and axis. The application of this information in a clinical setting has not been entirely successful because the optical measurements of the eye and the intervention methods are not exact.

Another area of interest is the relatively mature process of calculating the intraocular lens (IOL) power for post cataract patients. The calculation of implantable lens powers and prediction of post-operative outcomes has been an ongoing research interest since the first implanted lens. The calculations employed by modern strategies may effectively reduce the prediction error bias for the majority of normal cases but even with these adaptive third-generation IOL calculations, there are a significant number of real world cases whose outcomes are poorly predicted. A particular category that is poorly predicted is cataract surgery following previous refractive surgery. A primary source of error in the corneal power measurement with keratometers is that these instruments typically measure corneal curvature in the 32 mm zone and can miss the relatively flat central region. Modem IOL calculation strategy, as stated above, is based on calculations involving a mix of parameters intended to improve the effective lens position predictor (ELP) and calculation. Attempts to improve ELP have employed such parameters as axial length, eomeal power, horizontal corneal diameter, anterior chamber depth, crystalline lens thickness, preoperative refraction, and age. The basic methodology for the modern IOL calculation strategy has three steps: a) compute the ideal theoretical power of the implanted lens (this lens power will not necessarily be available) using measured and adapted optical model parameters, b) for the surgeon selected available power near the ideal power, predict the post operative refractive outcome, and c) given the actual outcome of the procedure, update optical model parameters to decrease the prediction error of future surgeries. As stated above, such modern strategies, while improving the prediction error bias for the majority of normal cases, do not improve predicability for many other cases, such as the case of cataract surgery following previous refractive surgery. One modern attempt at improvement is custom LASIK using corneal topography and/or wavefront aberration data. However, large amounts of positive spherical aberration can be induced as a result of LASIK procedures and for large pupil diameters, the retinal image quality may be degraded.

While past and current developments have improved the predictability of optical correction of aberrations in the human eye, as may be understood by those skilled in the art, the presently known techniques or methodologies have not produced a measure of predictability for the many variations found in the parameters describing the human eye.

SUMMARY OF THE INVENTION

The inventive principles of the advanced vision intervention algorithm (AVIA), as disclosed in the description of the preferred embodiment, may be used to improve the predictability of most known methodolgies for optical vision correction and may be applied to any similar methodology which may be developed, The advanced vision intervention algorithm (AVIA) provides a means to optimize the predictability of almost any current or anticipated customized human vision intervention method. In the following summary and Description of a Preferred Embodiment, AVIA is described in general terms in a series of steps. For the purpose of explanation, the AVIA method is shown in nine steps but as would be known by those skilled in the art, the number of steps used to describe the invention may be varied without departing from the principles of the disclosed invention.

For the example shown in the preferred embodiment, a summary of these steps is:

1. Input data: The input data is evaluated for obvious errors. Individual classes are used for each data type so that new data types and their evaluation methods are easily added to the framework. This includes inputting a set of categorical data for an eye and visual correction method and inputting a set of continuous data for an eye and visual correction method. The input data expresses the patient's visual correction need in terms of wavefront aberration. If the wavefront aberration is not explicitly measured using a system intended for this purpose, it may be estimated using the information provided such as spectacle 2. Build Optical Model: The second step is building an optical model of the eye and visual correction method that has been adapted based on prior visual correction outcomes. This processing step employs a ray transfer element (RTE) that is described in detail below. The RTE is an important component of AVIA.

3. Generate Initial intervention recommendation. In this step an initial intervention recommendation is computed based upon the optical model. This recommendation will either be categorical (e.g., selection from a series of available implantable lenses); a continuous scalar such as a theoretical power value; or a continuous vector quantity such as a surface description, or a combination of these such as a lens series with a discrete set of base curves and a customizable front surface.

4. Outcome Prediction: In this step, the outcome of the intervention is predicted in terms of the wavefront aberration, The predicted wavefront aberration is displayed in a number of ways any one of which can be selected by the surgeon for viewing. Examples of these displays include equivalent spectacle correction, wavefront aberration variance, wavefront aberration contour map, point spread function metrics and displays, modulation transfer function metrics and displays, and simulated retinal images.

5. Predicted Outcome Evaluation: In this step the surgeon uses the various displays of the predicted outcome wavefront aberration to decide if the outcome would be acceptable for the current case under consideration.

6. Intervention Design Iteration: In this step, the surgeon may continue iterating a modification of the Intervention plan and re-evaluates the predicted outcome until the predicted outcome is judged as acceptable.

7. Perform Intervention: In this step the surgeon performs the intervention.

8. Evaluation of Outcome: In this step the outcome of the intervention is assessed using data such as wavefront aberration exams, uncorrected and best corrected visual acuity, contrast sensitivity test, post-intervention spectacle correction, etc.

9. Update Historical Database: In this step the database of historical visual correction cases is updated to include the current case.

DESCRIPTION OF A PREFERRED EMBODIMENT

Figure 1:
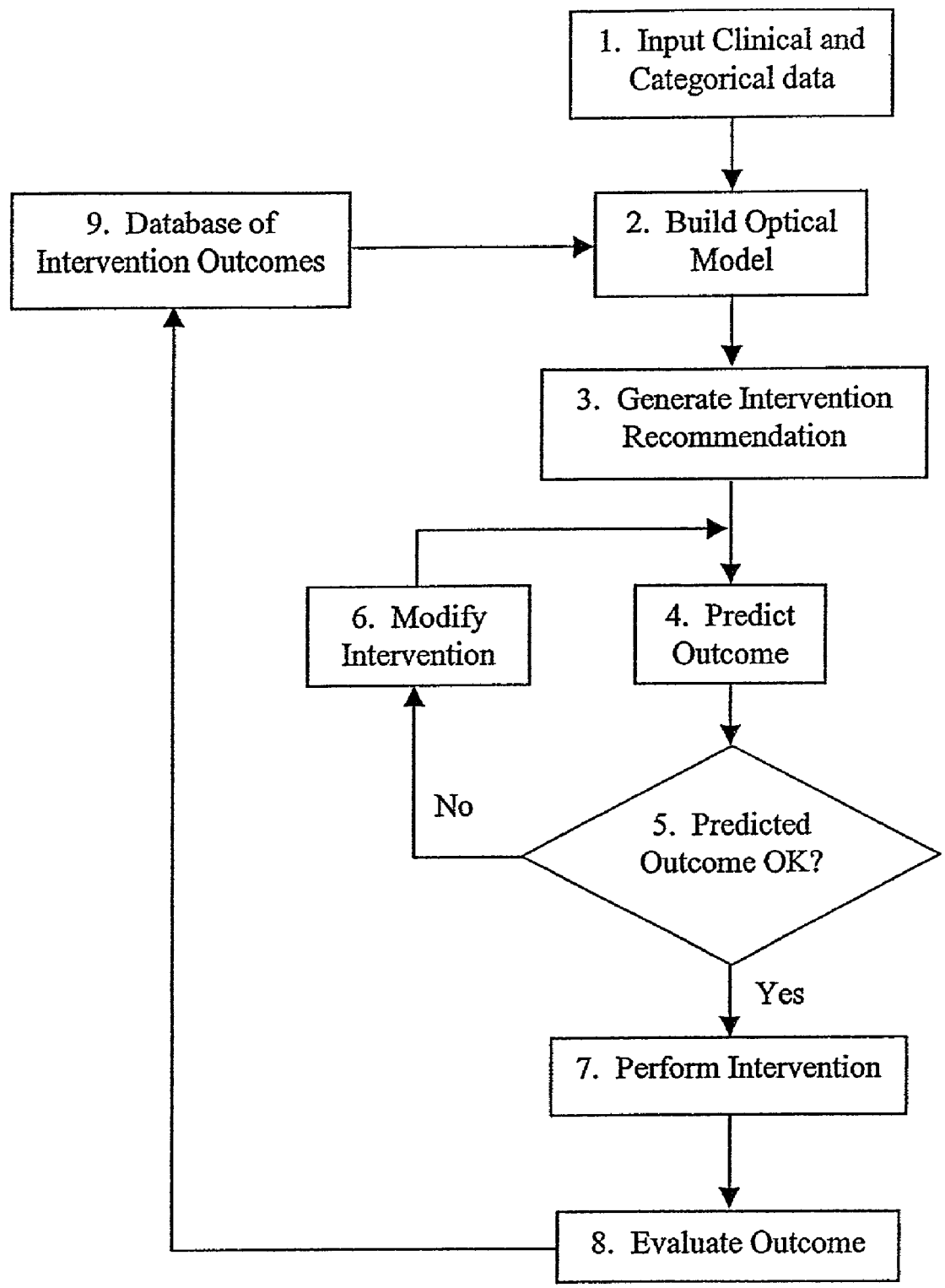
FIG. 1 shows in a block element flow diagram, the method of a preferred embodiment, according to the disclosed inventive principles.

The invention, according to its inventive principles, is disclosed with reference to the preferred embodiment, as described below, and with reference to the accompanying drawings. As shown in step 1 in FIG. 1, the first step uses the clinical and categorical data of the eye to construct an optical model, as shown in FIG. 2, and in step 2 of FIG. 1.

Optical Model

The foundation of the optical calculations and predicted outcome of a given intervention strategy is the optical model. The optical model is created using all available data for a given eye. This data could be as simple as the two basic quantities of keratometric data and spectacle correction or as complex as specifying multiple surfaces, axial locations, and wavefront aberration data, or additional input data, without departing from the disclosed inventive principles. To explain the procedure, a simple model consisting of a corneal surface and wavefront aberrations only, is used. In FIG. 2 is shown the cornea and wavefront W positioned along an optical axis. In this FIG. 2, the wavefront is located at the entrance pupil of the eye. As shown in FIG. 2, if a ray R2 is traced from the fovea, it would appear to exit the eye in the direction of R0. This exiting ray is perpendicular to W as shown by the dotted line intersection with W.

Figure 2:
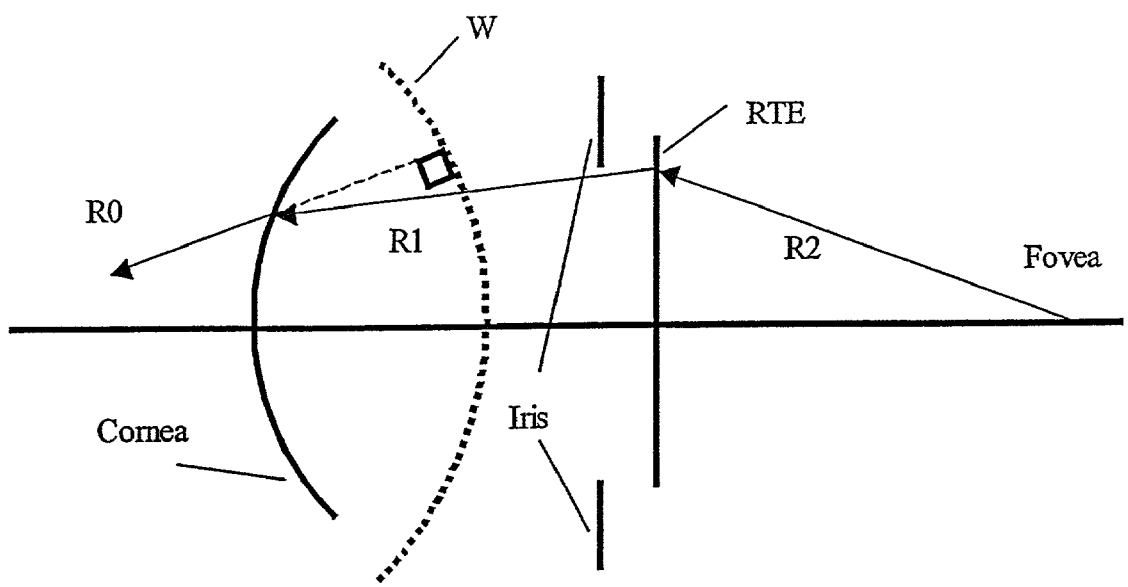
FIG. 2 shows in a simplified optical system for the human eye, how step 2, as described in the Summary and Description of a Preferred Embodiment and shown as numeral 2, in FIG. 1, for the modeling and use of a RTE.

To construct a model consistent with this information an average axial length of 24 mm may be assumed and a ray transfer element (RTE) introduced that maps an incoming ray R2 from the fovea to the intermediate ray R1 so that the exit ray RO has the desired orthogonality relationship with W, as shown in FIG. 2.

Construction of the RTE is accomplished using the following steps:

1. For a regular sampling of points on W do the following steps:

2. Construct the ray RO perpendicular to W at the sample point on W;

3. Trace—RO through the system until it intersects the RTE plane;

4. At the RTE intersection point, compute the mapping for the incident and transmitted rays;

and

5. If there are more samples on W go back to step 2.

The optical ray tracing of refractive and reflective elements is well known to those skilled in the art, and for that reason is not described in detail.

Ray Transfer Element

The ray transfer element (RTE) is an important aspect of AVIA. It provides both a means to generate an optical model that is consistent with exam data and a means to adapt the modeling to past surgical procedures so that prediction of postoperative outcomes is improved for future surgeries. The basic operation of the RTE is to efficiently map incident rays to transferred rays (either transmitted or reflected rays) and provide a method to smoothly adjust the mapping between data points to simulate continuous data. Primary operations on the RTE include ray intersection and ray reflection and transmission. The physical structure of the RTE is modeled as a plane with an aperture. Usually the aperture is circular, so the RTE looks like a circle of zero thickness in space. In local coordinates the RTE is represented as a plane equation with a separate test for the aperture. The equation of the planar object In local coordinates is simply $$Z=0 \tag{1}$$

The intersection of the RTE with a ray is straightforward. Let a ray in local coordinates be defined In (2).

$$\begin{bmatrix} x \\ y \\ z \end{bmatrix} = \begin{bmatrix} x_0 \\ y_0 \\ z_0 \end{bmatrix} + t \begin{bmatrix} x_d \\ y_d \\ z_d \end{bmatrix} \tag{2}$$

Then the intersection of the ray with the plane may be found, as in equation (3).

$$\begin{bmatrix} x \\ y \\ 0 \end{bmatrix} = \begin{bmatrix} x_0 \\ y_0 \\ z_0 \end{bmatrix} - \frac{z_0}{z_d} \begin{bmatrix} x_d \\ y_d \\ z_d \end{bmatrix} \quad (3)$$

where $Z_d=0$. Given the location of the planar Intersection (x,y,0), a final test is made to ensure the point is inside the aperture region.

RTE Construction

Figure 3:
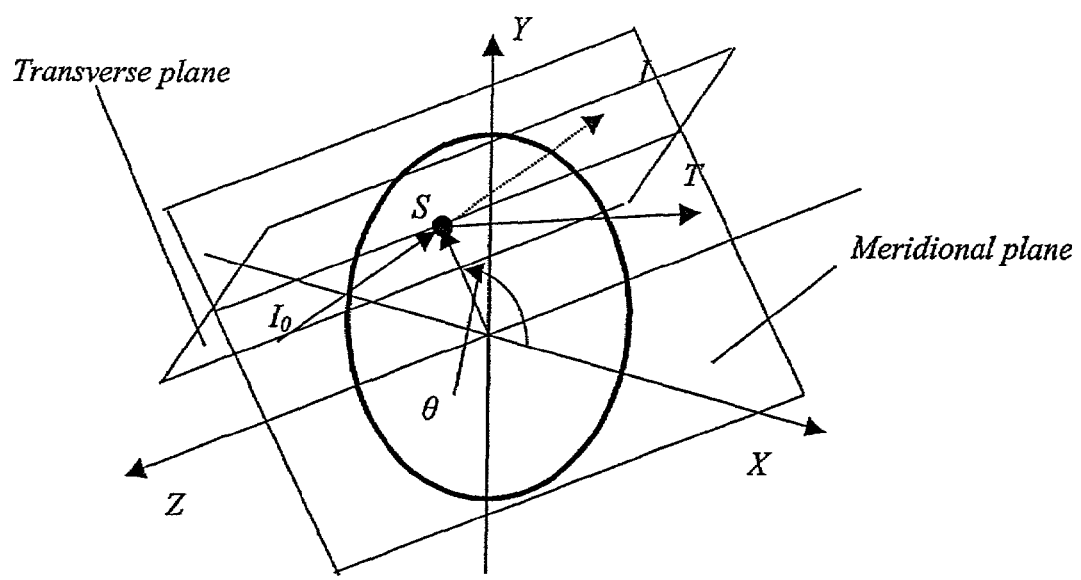
FIG. 3 shows an intersection point of an incident ray 1, and the RTE referenced to the meridional and transverse planes.
Figure 4:
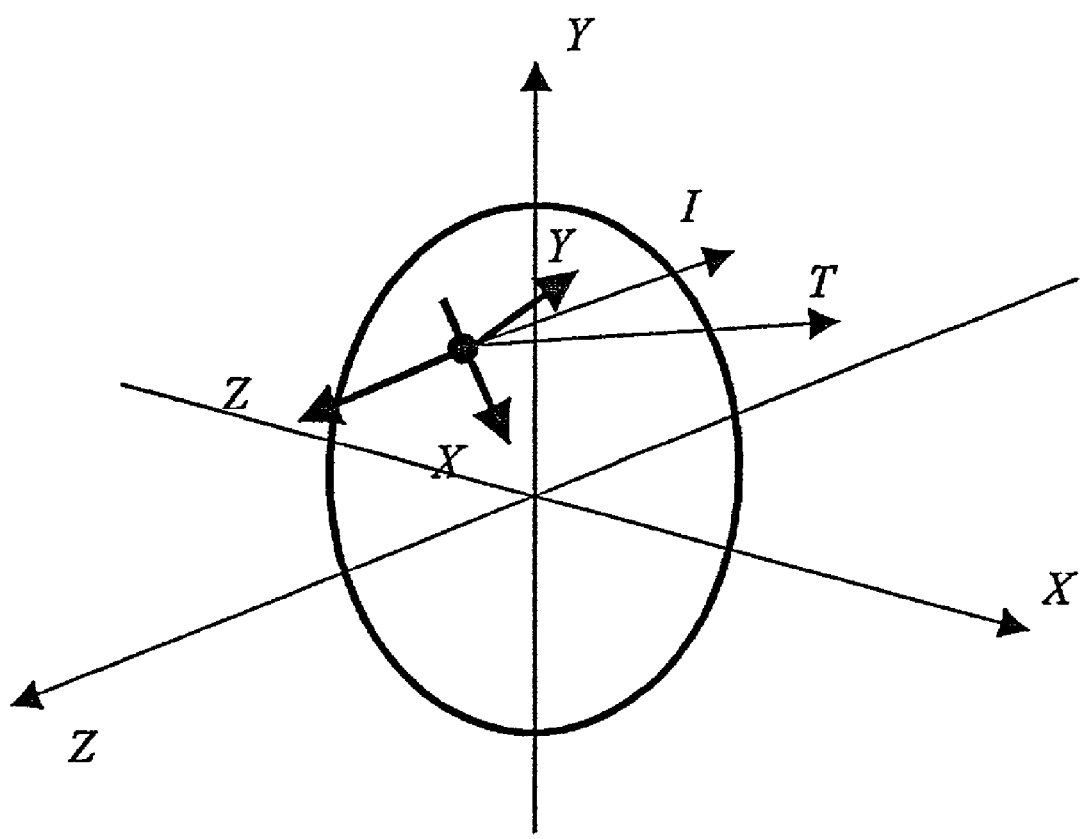
FIG. 4 shows the basis vectors for the meridional coordinate system of FIG. 3.

In the preferred embodiment, the construction of the RTE is described in local coordinates. In practice, rays defined in world coordinates are first transformed into local coordinates using homogeneous transformation matrices, collectively called a world-to local transformation matrix. Likewise, resulting rays in local coordinates are transformed to world coordinates using an inverse of the previous homogeneous transformation matrix, called local-to-world transformation matrix, as would be well known to those skilled in the art Since the goal of the RTE is to transform an input ray into an output ray for a given intersection point, we simply construct a mapping for a set of input/output ray pairs. Suppose an incident ray I and a transmitted ray T defined in local Coordinates is given. The intersection point (x,y,0) is denoted S. The plane that contains the optical axis (z-axis) and the point S is called the meridional plane. The plane parallel to the z-axis and perpendicular to the meridion at plane is referred to as the transverse plane. These planes are illustrated in FIG. 3. The strategy for finding the mapping of I to T is to find the change in elevation and azimuth angles for the two rays with respect to the meridional and transverse pianos, so that I can be rotated into T. The first step is to compute a meridional plan coordinate basis matrix. For this coordinate system, X' points from S to the origin. Y is 90 deg counter clockwise to X', and Z' is parallel to the original z-axis. These basis vectors are illustrated in FIG. 4.

For simplicity of presentation, in the following the prime notation is dropped for the meridional basis vectors X', Y', and Z'. Given S we can compute the meridional coordinate basis matrix by finding the X, Y and Z vectors as in equation (4).

$$X = \frac{S}{\|S\|}, Y = \begin{bmatrix} -X_2 \\ X_2 \\ 0 \end{bmatrix}, Z = \begin{bmatrix} 0 \\ 0 \\ 1 \end{bmatrix} \quad (4)$$

If the norm of S is zero, the intersection point is at the origin, i.e., on the optical axis. In this case X in equation (4) is taken as being along the x-axis. Using this the meridional coordinate basis matrix M can be written as In (5).

$$M = \begin{bmatrix} X_1 & Y_1 & Z_1 \\ X_2 & Y_2 & Z_2 \\ X_3 & Y_3 & Z_3 \end{bmatrix} \quad (5)$$

To compute the desired rotation angles between I and T, first rotate the vectors using the meridional coordinate basis M as in (6).

$$I_{M=M}{}^T I$$

$$T_{M=M}{}^T T \quad (6)$$

In (6) and in the following discussion, the vectors I and T are first normalized to unit length. Now, can be computed the rotation angle for each of these vectors to the meridional coordinate x-axis. Also can be computed the rotation angle between the XZ plane and each of these vectors. These calculations are made using equations (7) and (8), respectively.

$$\theta_A = \tan^{-1}\left(\frac{A_z}{A_x}\right) \quad (7)$$

$$\alpha_A = \tan^{-1}\left(\frac{A_y}{\sqrt{A_x^2 + A_z^2}}\right) \quad (8)$$

In equations (7) and (8), A stands for either the vector I or T. The arc tangent function indicated in these equations is conveniently computed using the a atan2 function in C++ to automatically handle all possible values of numerator and denominator around the unit circle including the case of denominator equal to zero. After these two elevation angles and two azimuth angles have been computed, the difference can be computer as indicated in (9). These are the angles stored to map an incident ray direction to the transferred ray direction.

$$d\theta = \theta_I - \theta_T$$

$$d\alpha = \alpha_I - \alpha_T \quad (9)$$

To summarize, for a given intersection point S, compute and save the elevation and azimuth angles $d\theta$ and $d\alpha$ and do required to rotate the incident vector I into the direction of transferred vector T. All of the forgoing calculations would be known to those skilled in the art and for that reason are not described in detail. Discussed next, is the use of the RTE to map an input vector to an output vector. This illustrates the case of forward ray tracing. The case of reverse ray tracing is similarly computed, as would be known to one skilled in the art and is omitted for brevity.

RTE Optical Ray Tracing

To perform an optical ray tracing of the RTE, first find where an incident vector I is intersected with the RTE at location S. This intersection point is computed using equation (3). Given this intersection point, the transmitted vector T is easily computed. In general, the intersection point S will not correspond to a previous constraint point, so some type of interpolation will be required. Two strategies to accomplish this are (1) to compute a least squares approximation function fit (e.g., 2D polynomial or 2D B-Spline) for each of the azimuth and elevation angles or (2) to perform a Delaunay triangulation of the intersection points in the XY plane and interpolate the points to obtain the angles. As would be known to those skilled in the art . . . , Suitable software may be developed for performing these calculations on a general purpose computer. The computation of T (which produces a ray tracing of the RTE) is performed as follows:

1. Intersect I with the RTE to find S
2. Apply the transformations indicated in (4) to (6) and then rotate I by the azimuth and elevation angles associated with S. This rotated vector represents T in meridional coordinates.
3. Apply the inverse coordinate transformation to T.

The adjustment angles dθ and dα are applied to the angles interpolated in step 2 of the algorithm. This provides a method to adjust the optical model based on actual outcomes. In a similar way, a paraxial power value could be assigned to the projection of the I end T rays onto the meridional and transverse planes. This alternate scheme has the benefit of describing the bending of rays in units of diopters that are familiar to visual optics professionals.

Strategy for RTE Updating Based on Historical Cases

A strategy for updating the RTE portion of the optical model is based on the evaluation of historical cases. In a preferred embodiment, as described in this application, first examine the historical database for similar cases to a given present case under consideration. This similarity is measured in terms of both categorical data and continuous data. Categorical data such as surgeon, sex, intervention procedure. etc., should be matched closely by all historical cases to be similar to the current case. This is accomplished by filtering the database for all records that match the same categories. Continuous data such as preoperative spectacle correction, corneal thickness, etc., is measured using a weighted Euclidean distance. Each of the 5 continuous data is normalized so that the mean and standard deviation of each random variable is zero and one, respectively. Only the N closest cases from the historical database are used to compute the RTE adaptation parameters. A reasonable value for the integer N may be determined during a first evaluation (described below).

The RTE update algorithm is then:

1. Establish the categorical data for the current case under consideration and identify the continuous data.

2. Filter the historical database so that we only consider cases in the same category.

3. For all filtered records, find the N closest records using normalized distances.

4. For these N closest records, find the average back-calculated RTE for the actual postoperative wavefront aberration (See RTE Arithmetic Operations below.)

5. Use the average of the RTE deltas in the Optical Modeling of the current case It is often possible to have the case of time-varying parameters, that is, cases where the statistics slowly vary over time. To account for this in our calculations of the updated RTE, a weighting may be applied to the average calculation ab that older cases are not weighted as much as more recent cases.

RTE Arithmetic Operations

RTE arithmetic operations that help facilitate AVIA calculations are:

Addition, subtraction, multiplication, and division of two RTEs.

Addition, subtraction, multiplication, and division of an RTE and a scalar.

These operations (addition, subtraction, multiplication, and division) on two RTEs are performed in a point-wise fashion. In general, the stored sample points from two RTEs will not be in the same locations, so one or both of the sample point arrays must be interpolated to obtain points at matching locations.

These operations (addition, subtraction, multiplication, and division) on a RTE and a scalar are also performed in a point-wise fashion. In this case there is no need to interpolate to align sample points as the same scalar operation is applied to all points in the RTE.

Implementation of the RTE using the C++ programming language permits these operations to be specified directly using standard symbols of "+", "−"," "*", and "I". This makes the generation and maintenance of RTE aware programs very efficient. For example, the mean of four RTEs can be expressed as:

$$MR = \frac{(R1 + R2 + R3 + R4)}{4} \tag{10}$$

Using an appropriate class implementation of a RTE, this expression is a valid C++ statement and its intent is easily understood.

I claim:

1. A method of intervention for correcting vision in an eye of a patient caused by defects in the eye, said method being performed with the aid of a computer system, said method comprising the steps of:
   (a) inputting categorical data for an eye of the patient with visual correction methods and outcomes;
   (b) inputting continuous data for said eye with visual correction methods and outcomes;
   (c) examining said eye and building an optical model of said eye including mapping input light rays and output light rays having a given intersection;
   (d) comparing said model with said categorical and said continuous data with visual correction methods and outcomes;
   (e) generating a procedure for said eye with a predicted outcome;
   (f) comparing said predicted outcome with said categorical and continuous outcomes to determine acceptability; and
   (g) performing said procedure when the predicted outcome is acceptable.

2. The procedure of claim 1 including the steps of iterating modifications of said procedure and comparing said predicted outcomes until a predicted outcome is acceptable.

3. The procedure of claim 1 including the step of inputting data from said eye including visual correction method and outcome, and evaluating the outcome on said eye.

4. The procedure of claim 1 wherein said computer system includes a display means for viewing said predicted outcome.

5. The procedure of claim 1 wherein a ray transfer element (RTE) is provided for converting said categorical and said continuous data to wavefront aberrations.

6. The procedure of claim 5 wherein said categorical and said continuous data include wavefront aberrations of past surgical procedures, thereby improving projections for subsequent procedures.

7. A method of optimizing the predictability of a vision correction method comprising the steps of:
   (a) inputting a set of categorical data points for an eye with visual correction methods;
   (b) inputting a set of continuous data points for an eye with visual correction methods;
   (c) inputting outcome data points for visual correction methods;
   (d) examining a patient eye and building a model of said patient eye, said model based on optics within said patient eye;
   (e) selecting a visual correction method for said patient eye based on said outcome data and generating an initial procedure recommendation;

(f) predicting the outcome of said initial procedure recommendation for said patient eye;

(g) evaluating said predicted outcome for acceptability; and (h) iterating a modification of said initial procedure recommendation and re-evaluating the predicted outcome until predicted outcome is acceptable.

8. A method of optimizing the predictability of a vision correction method of claim 7 including the steps of:

(a) performing the procedure on said patient eye;

(b) evaluating the outcome of said procedure; and (c) updating data points.

9. A method of optimizing the predictability of a vision correction method of claim 7 comprising the steps of:

(a) said examining including providing an incident light ray to said eye, said incident light ray transmitted by said eye at an angle, said incident light ray and said transmitted light ray having an intersection point in a meridional plane; and (b) computing the difference in elevation and azimuth between said incident ray and said transmitted ray to rotate said incident ray to coincide with said transmitted ray.

10. A method of optimizing the predictability of a vision correction method of claim 7 comprising the steps of:

(a) evaluation of historical cases for similar data in terms of categorical and continuous data;

(b) select closest historical cases;

(c) average the actual postoperative outcome of said selected cases; and (d) apply said average to said optical model.

11. A method of constructing a model of the eye for improved vision utilizing optical projections comprising the steps of:

(a) establishing a wavefront for an eye;

(b) providing a planar ray transfer element (RTE) oriented generally normal to the optical axis of said eye for passage of an incident light ray into said eye resulting in an outgoing light ray having an exit point in said eye;

(c) locate the intersection point of said incident light ray and a vector orthogonically intersecting said wavefront from said exit point;

(d) extending said vector to intersect said RTE;

(e) compute the mapping change in elevation and azimuth angles at said RTE necessary to rotate said incident ray to coincide with said vector and improve vision.

* * * * *